(12) United States Patent
Milanese

(10) Patent No.: US 11,844,477 B2
(45) Date of Patent: Dec. 19, 2023

(54) TREATMENT DEVICE FOR WALKABLE SURFACES, AS FOR EXAMPLE FLOORS

(71) Applicant: PLASTECS SRL, Susegana (IT)

(72) Inventor: Pier Antonio Milanese, Susegana (IT)

(73) Assignee: PLASTECS SRL, Susegana (IT)

( * ) Notice: Subject to any disclaimer, the term of this patent is extended or adjusted under 35 U.S.C. 154(b) by 293 days.

(21) Appl. No.: 17/295,203

(22) PCT Filed: Dec. 5, 2019

(86) PCT No.: PCT/IT2019/050255
§ 371 (c)(1),
(2) Date: May 19, 2021

(87) PCT Pub. No.: WO2020/115780
PCT Pub. Date: Jun. 11, 2020

(65) Prior Publication Data
US 2022/0007914 A1    Jan. 13, 2022

(30) Foreign Application Priority Data

Dec. 7, 2018 (IT) .......................... 102018000010902

(51) Int. Cl.
*A47L 11/00* (2006.01)
*A47L 11/40* (2006.01)
(Continued)

(52) U.S. Cl.
CPC ......... *A47L 11/4088* (2013.01); *A47L 11/302* (2013.01); *A47L 11/4005* (2013.01);
(Continued)

(58) Field of Classification Search
CPC ........ A47L 11/02; A47L 11/03; A47L 11/085; A47L 11/145; A47L 11/185;
(Continued)

(56) References Cited

U.S. PATENT DOCUMENTS

2016/0360943 A1* 12/2016 Krebs ..................... A47L 13/44
2017/0049287 A1*  2/2017 Knutson .............. A47L 11/201

FOREIGN PATENT DOCUMENTS

AU    2018101242 A4 *  9/2018  ............... A47L 5/28
EP         3238596 A1    11/2017
(Continued)

OTHER PUBLICATIONS

International Search Report dated Mar. 23, 2020 in corresponding International Application No. PCT/IT2019/050255; 3 pages.

*Primary Examiner* — Katina N. Henson
*Assistant Examiner* — Alyssa R Williams
(74) *Attorney, Agent, or Firm* — Maier & Maier, PLLC

(57) ABSTRACT

Hand-guided treatment device for walkable surfaces adapted to clean, sanitize and dry such surfaces, including a guiding body joined below, through an articulated element to a unit for cleaning, sanitizing and drying such surfaces, the guiding body having housed inside it at least a control and command electronic circuit board powered by at least an electrical transformer, at least a first reservoir and at least an electrical pump. The unit has component elements assembly inserted into a stiff and shell-shaped casing, this latter being opened on its lower part and provided at its lower part with at least a free wheel, for moving the device, and being provided on its upper part with an upper opening, in correspondence of the articulated element, adapted to connect the component elements of the guiding body and component elements assembly.

11 Claims, 10 Drawing Sheets

(51) Int. Cl.
  *A47L 11/30* (2006.01)
  *A61L 2/24* (2006.01)
  *G05D 23/19* (2006.01)
  *H05B 1/02* (2006.01)
  *H02J 7/02* (2016.01)

(52) U.S. Cl.
  CPC ....... *A47L 11/4011* (2013.01); *A47L 11/4016* (2013.01); *A47L 11/4069* (2013.01); *A47L 11/4075* (2013.01); *A47L 11/4083* (2013.01); *A47L 11/4086* (2013.01); *A61L 2/24* (2013.01); *G05D 23/1917* (2013.01); *H05B 1/0244* (2013.01); *A61L 2202/14* (2013.01); *A61L 2202/17* (2013.01); *H02J 7/02* (2013.01); *H05B 2203/021* (2013.01)

(58) Field of Classification Search
  CPC .............. A47L 11/4011; A47L 11/4013; A47L 11/4041; A47L 11/408; A47L 11/4083; A47L 11/4086
  See application file for complete search history.

(56) References Cited

FOREIGN PATENT DOCUMENTS

| | | | |
|---|---|---|---|
| JP | H02-55028 A | 2/1990 | |
| KR | 101169069 B1 * | 7/2012 | ............... A47L 5/28 |
| WO | 97/28732 A1 | 8/1997 | |

\* cited by examiner

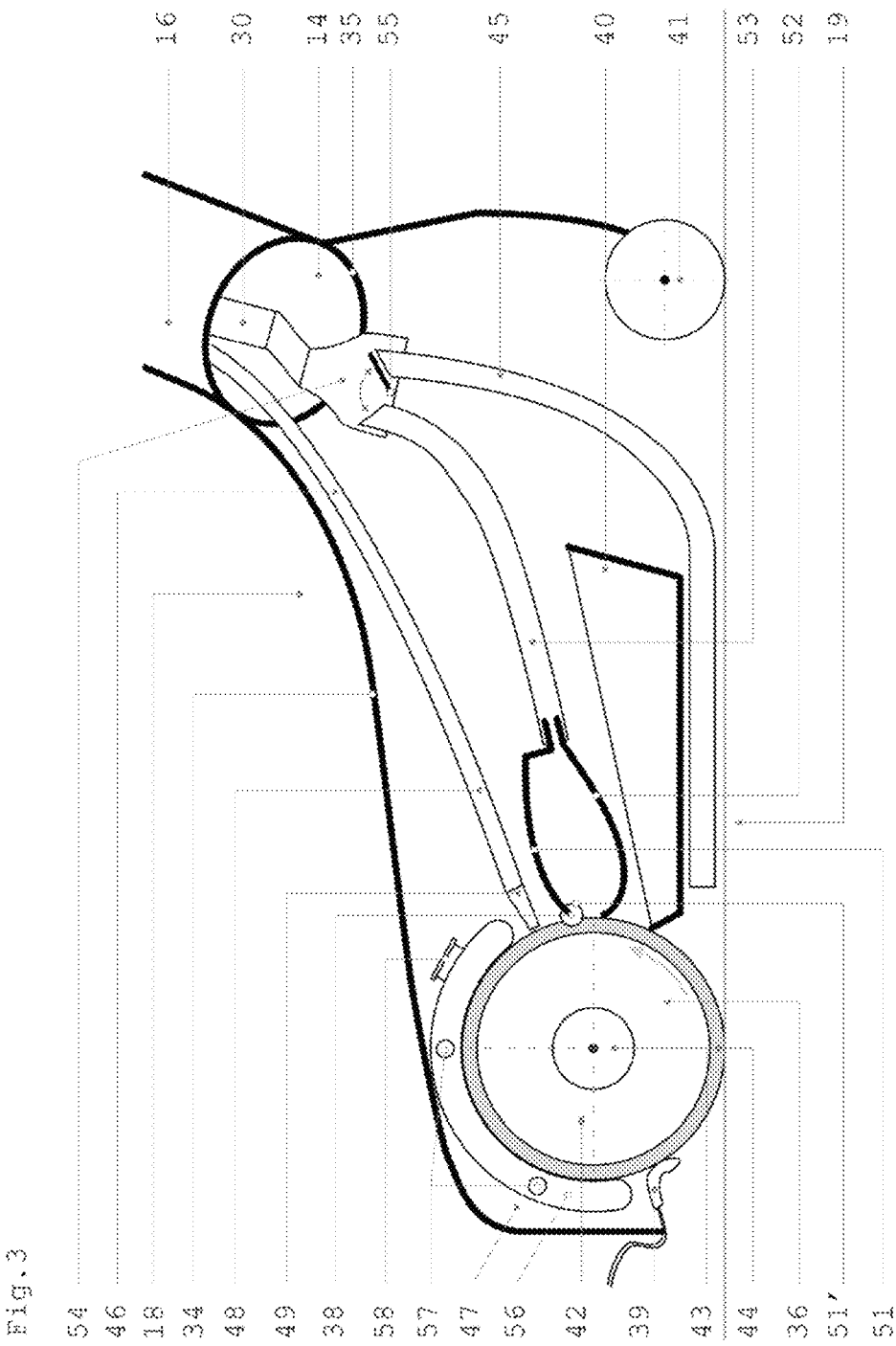

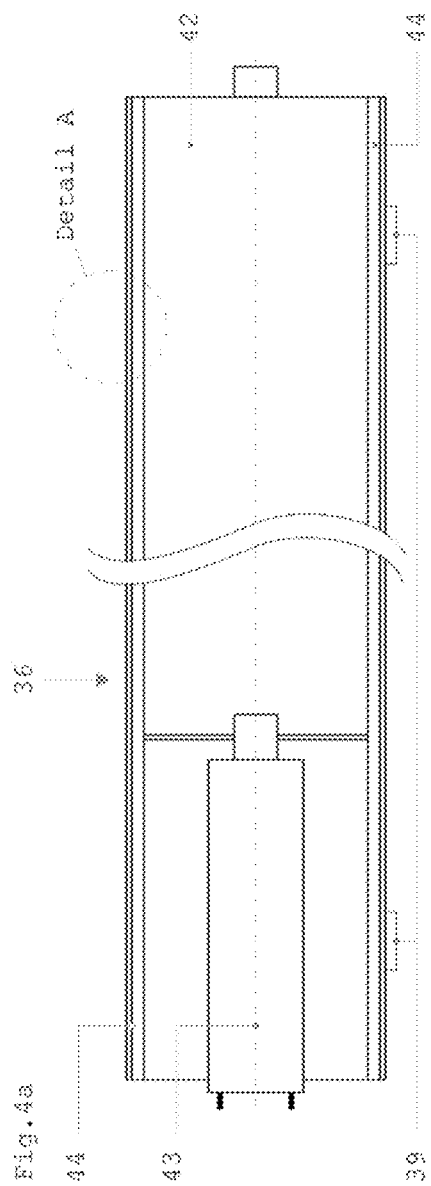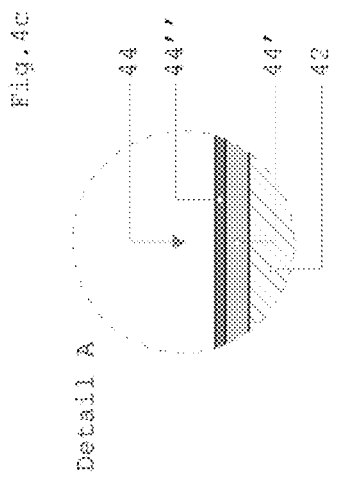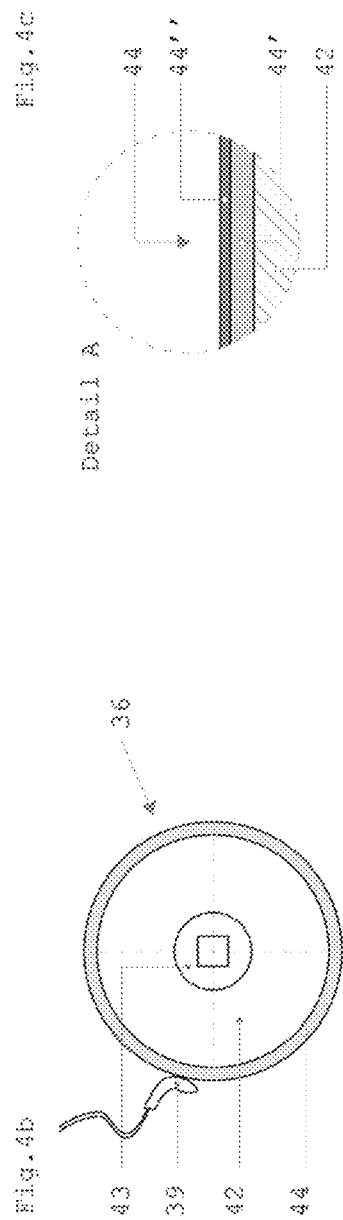

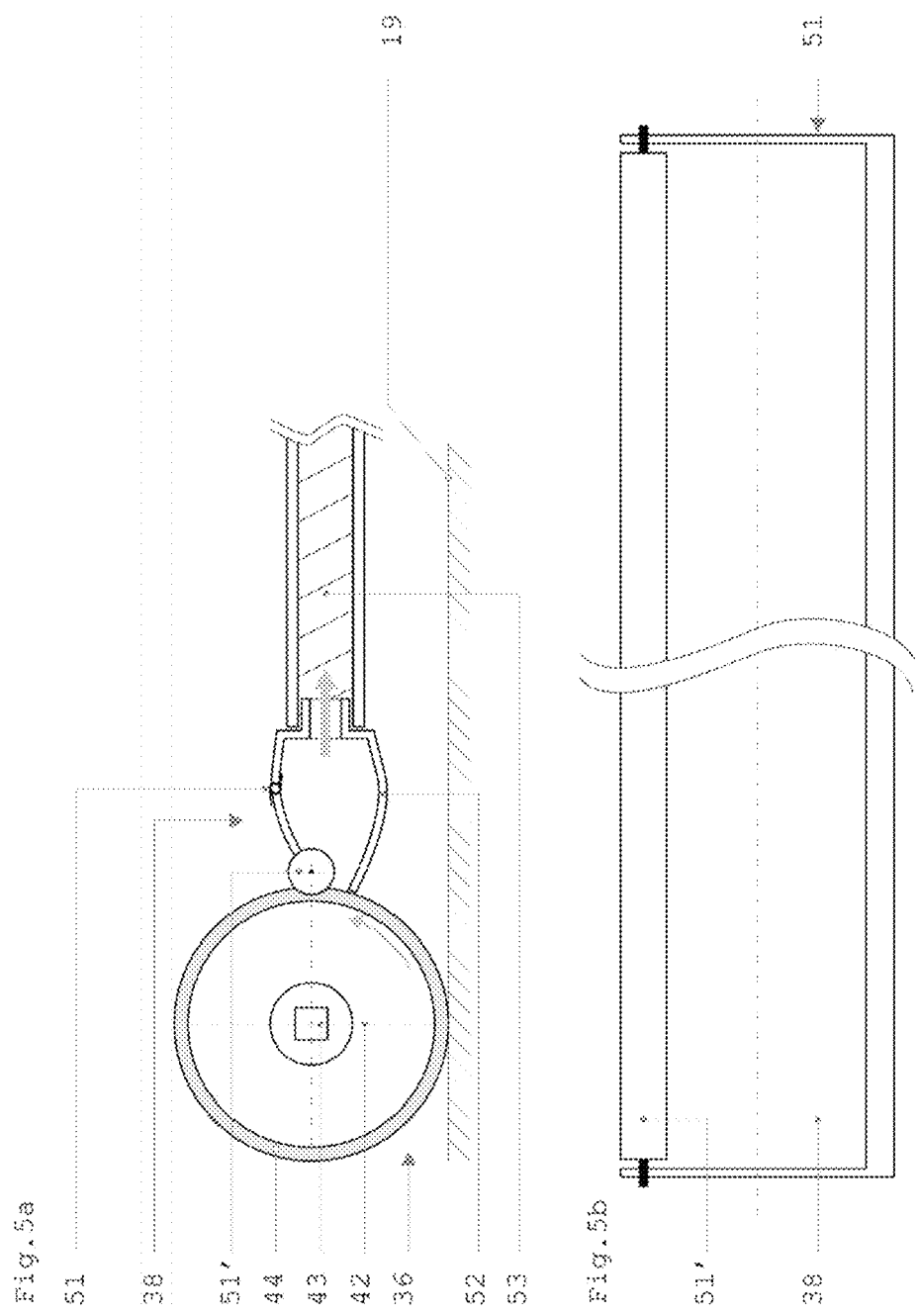

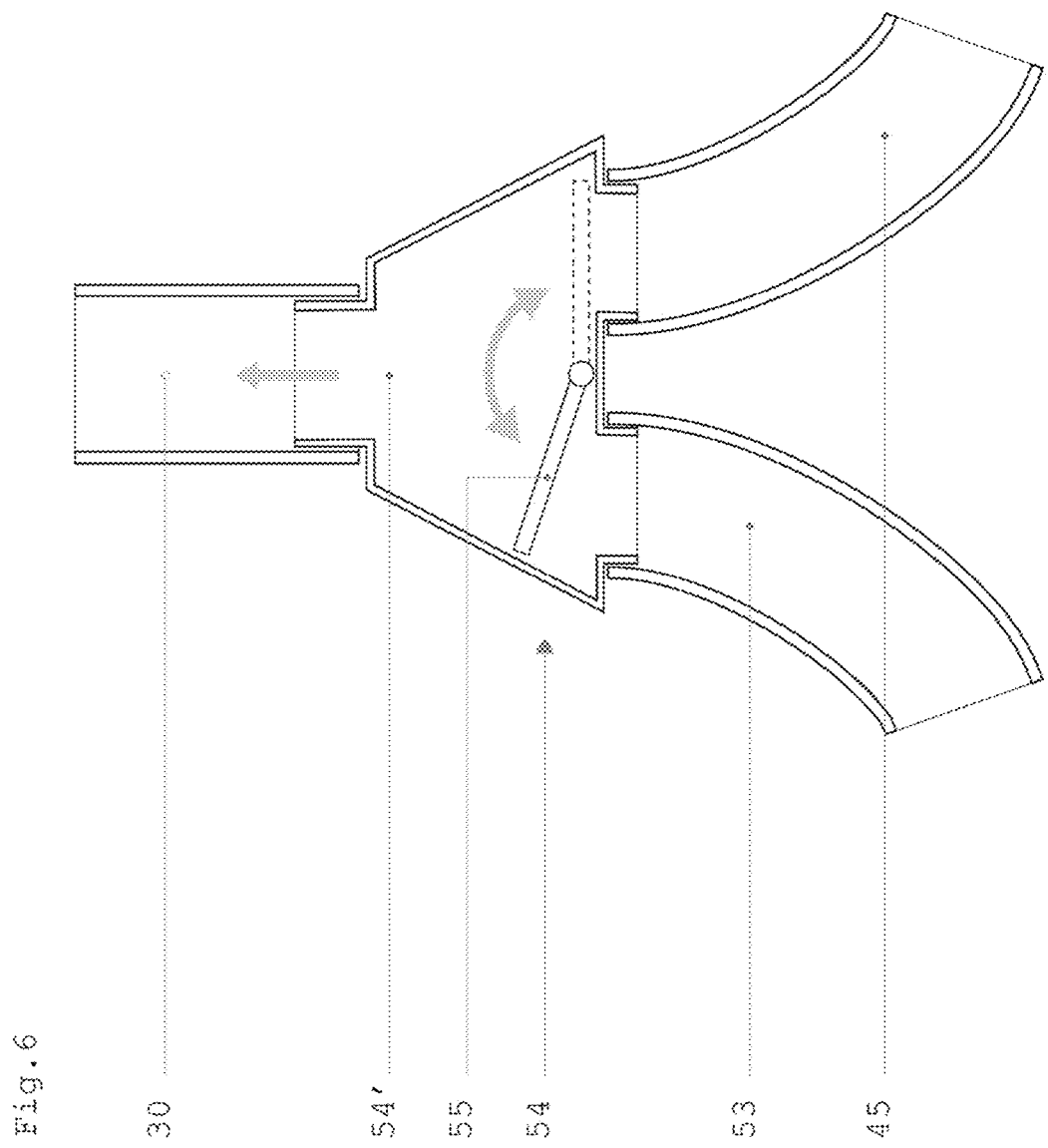

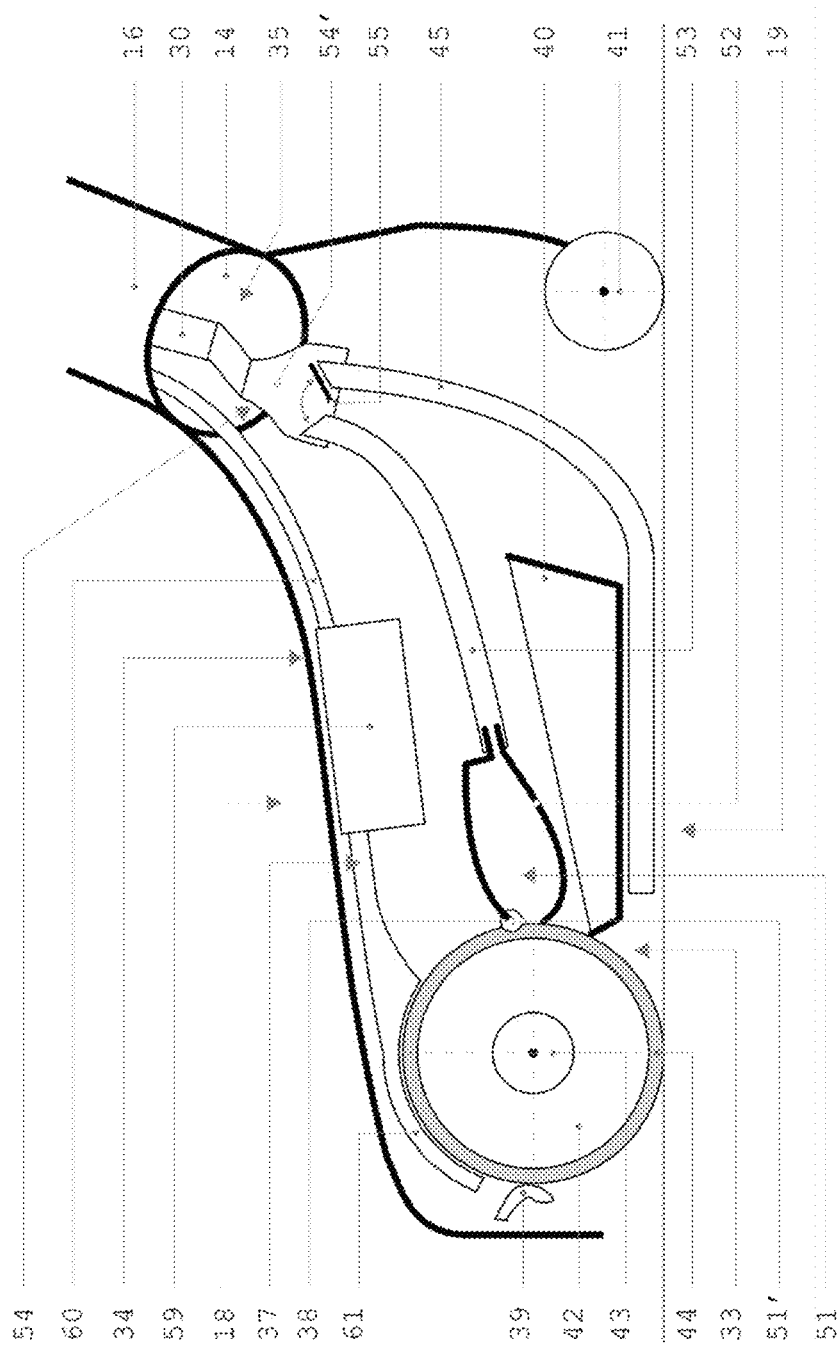

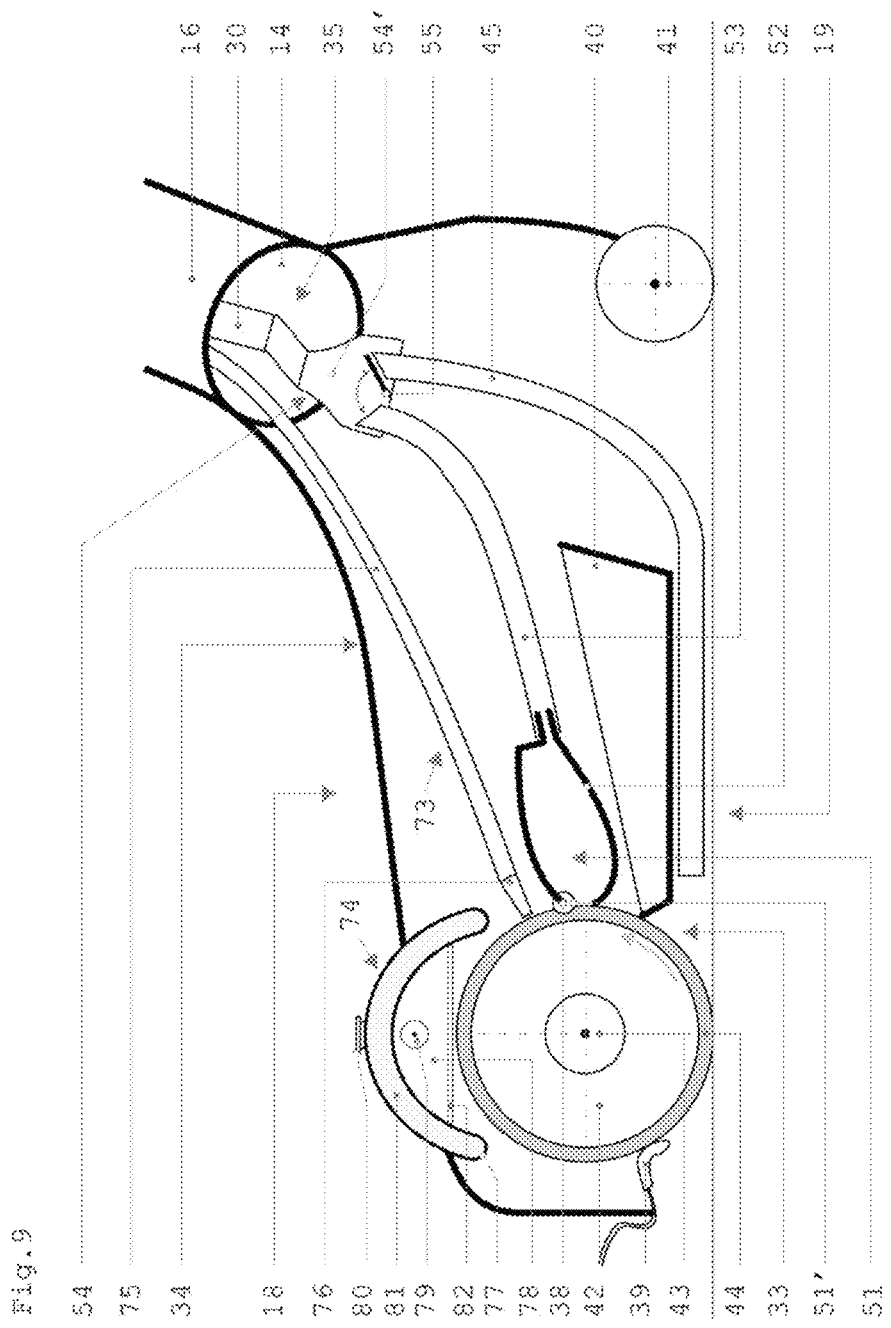

TREATMENT DEVICE FOR WALKABLE SURFACES, AS FOR EXAMPLE FLOORS

FIELD

The present invention concerns a treatment device for walkable surfaces, as for example floors.

BACKGROUND

At present, there are known cleaning apparatuses for floors provided with rotating cylindrical brushes, which are actuated by a motor, with a reservoir for water and a circuit such to allow to such a water to reach, at room temperature, and to wet said rotating brushes, for increasing the cleaning capacity of these latter.

Said cleaning apparatuses are eventually equipped with a suction unit, adapted to collect the water left on the floor by said rotating brushes after the cleaning.

Such cleaning apparatuses, working with cold water, carry out a cleaning action only, but not a sanitizing one of the floors, and moreover, by using bristle brushes, the water is distributed in a heterogeneous way, thereby being wasted in a great quantity. Furthermore, systems for dosing the water that arrive on to said rotating brushes are not provided.

As regards the collection of the water from the floor through a suction unit, it is easy to understand that it can't be adequate considering the above said problems, and therefore, the floor remains very wet also after such a sucking phase of the water, thereby requiring long time of drying.

SUMMARY

The object of the present invention is to realize a device for hot cleaning, sanitizing and drying of surfaces, as for example floors, that is able to overcome all the above said existing drawbacks.

BRIEF DESCRIPTION OF THE FIGURES

The invention will be better understood by the following description, given by way of a not limiting example only, and with reference of the attached drawings, in which:

FIG. 3 shows a schematic cross-sectional view of a group of component elements of the device of FIG. 1, in a first embodiment thereof;

FIGS. 4a-4b show a schematic top view and a side schematic view of two first component elements of the group of FIG. 3, respectively;

FIG. 4c shows an enlarged detail of FIG. 4a;

FIG. 5a shows a side view of second component elements of the group of FIG. 3;

FIG. 5b shows a top view of a component element of FIG. 5a;

FIG. 6 shows a schematic cross-sectional view of third components of the group 3;

FIG. 7 shows a schematic cross-sectional view of a group of component elements of the device of FIG. 1, in a second embodiment thereof;

FIG. 8b shows a perspective top view of the element of the FIG. 8a;

FIG. 9 shows a schematic cross-sectional view of a group of component elements of the device of FIG. 1, in a third embodiment thereof;

DETAILED DESCRIPTION OF THE EMBODIMENTS

In the following description and figures it is described a treatment device 15 for walkable surfaces, as for example floors, adapted to perform at the same time a cleaning and sanitizing action and an immediate drying action of the treated surface, while the operator manually moves it.

Figure 1:
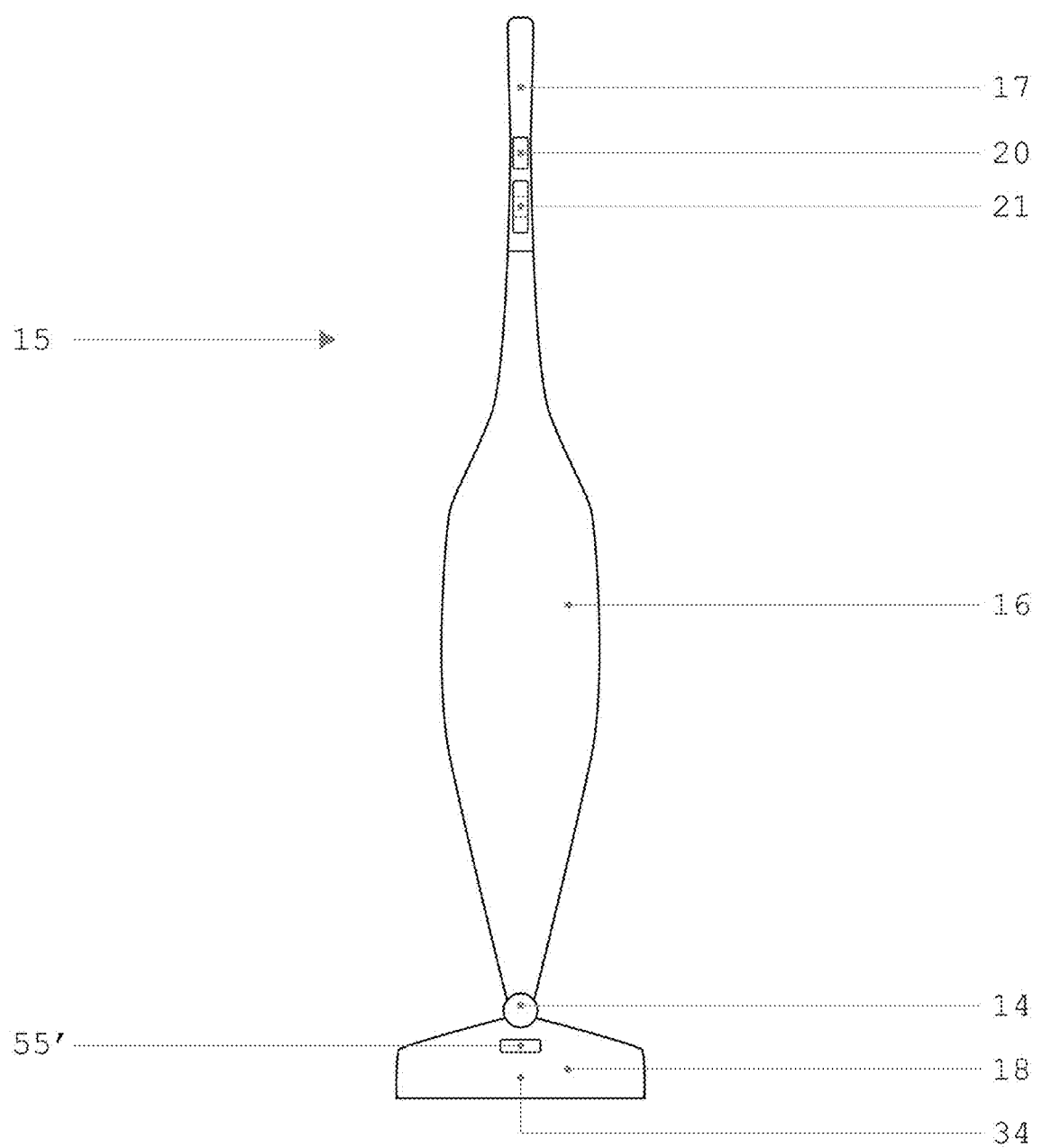
FIG. 1 shows a front view of the device for cleaning, sanitizing and drying surfaces, according to the invention.

Such a device 15, as visible in FIG. 1, is constituted by an upward extended guiding body ending with a control handgrip 17 and joined below in an articulated way, through an articulated element 14, as for example a universal joint, to a cleaning, sanitizing and drying unit 18 for surfaces 19. Such a handgrip 17 is provided with commands means 20 of the device 15, which are adapted to turn on and turn of such a device 15, by turning it from a rest state thereof to an operative state thereof and vice versa, and adapted to select the various pre-set operative functions, said handgrip 17 being also provided with at least a displaying means 21, as for example a display or a set of led, which is adapted to visualize the information about the operation of the device 15.

Figure 2:
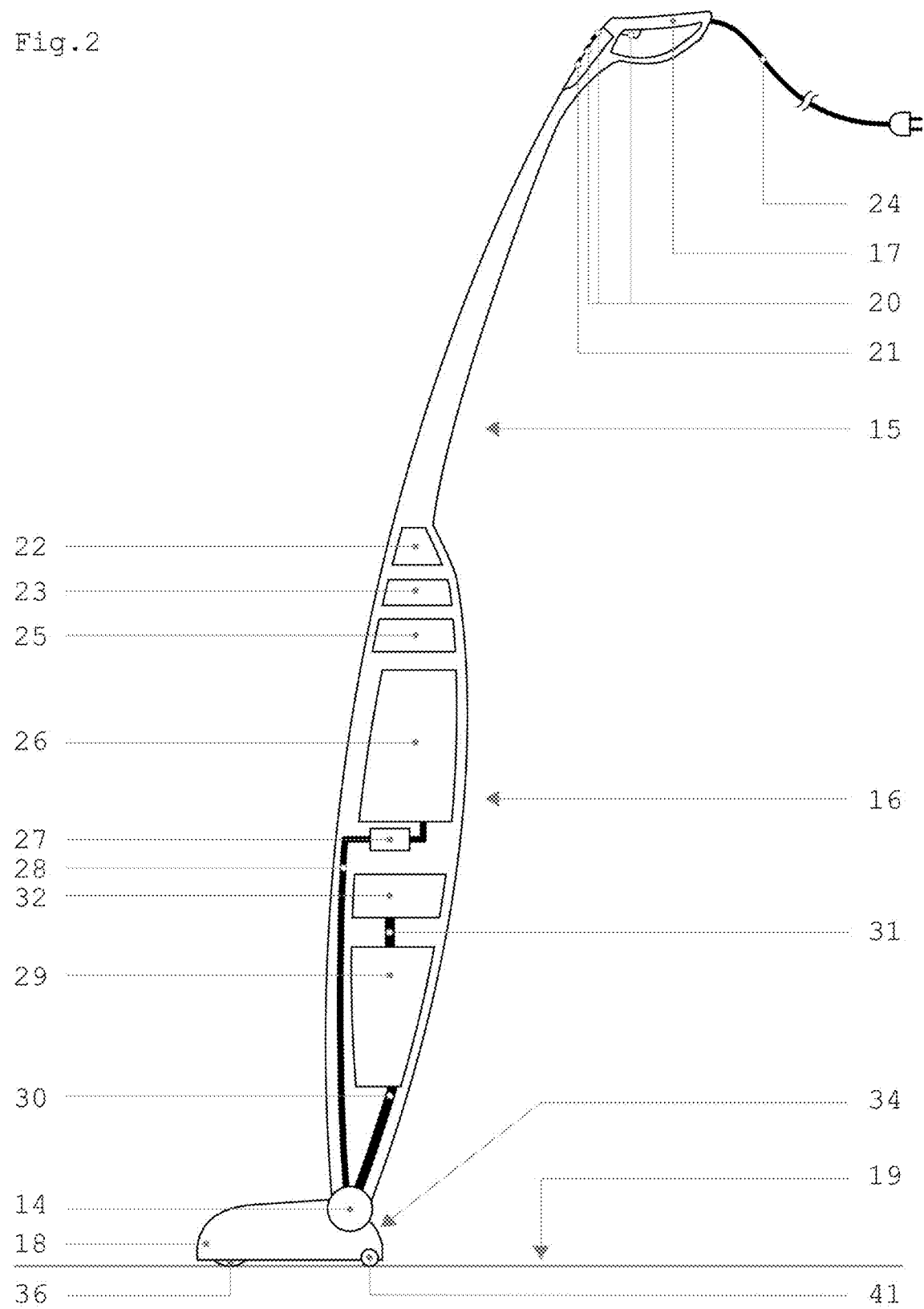
FIG. 2 shows a schematic cross-sectional view of the device of FIG. 1.

Referring to FIG. 2, which shows a schematic cross-sectional view of the device 15, it may be noted that inside the guiding body 16 there are housed at least a control and command electronic circuit board 22, at least an electrical transformer means 23 and at least a power supply means 25, as for example a battery.

Such a control and command electronic circuit board 22 is adapted to control and/or to command all the electric and electronic elements and/or components and/or means of the device 15 on the basis of pre-set parameters, which are selected through said actuation and selection means 20, and is powered the electrical transformer means 23, in turn connected to the power grid through a power cable 24 and/or to the battery 25.

Inside the guiding body 16 there are also housed at least a first and a second reservoir 26, 29, at least an electrical pumping means 27, as for example an electropump, and at least a an electrical vacuum means 32, as for example an electrical vacuum motor of the WD type. Said first reservoir 26 is adapted to contain cleaned cleaning liquids, as for example water, and able to be filled from outside through a closable opening (not shown), and is connected with its outlet to the electrical pumping means 27, that in turn is connected, through a flexible or stiff duct 28, to the inlet of the unit 18 and adapted to draw the liquid from said first reservoir 26 and to convey such a liquid into said unit 18, whereas the outlet of this latter is connected in succession by means of a duct 30 to the inlet of the second reservoir 29, adapted to contain the filth caused by the cleaning and the sanitizing and arranged preferably below with respect to the first reservoir 26, that in turn is connected at its outlet through a duct 31 to the electrical vacuum means 32, which is adapted to suck the filth after the treatment of the surface 19 and convey it into said second reservoir 29.

Figure 10:
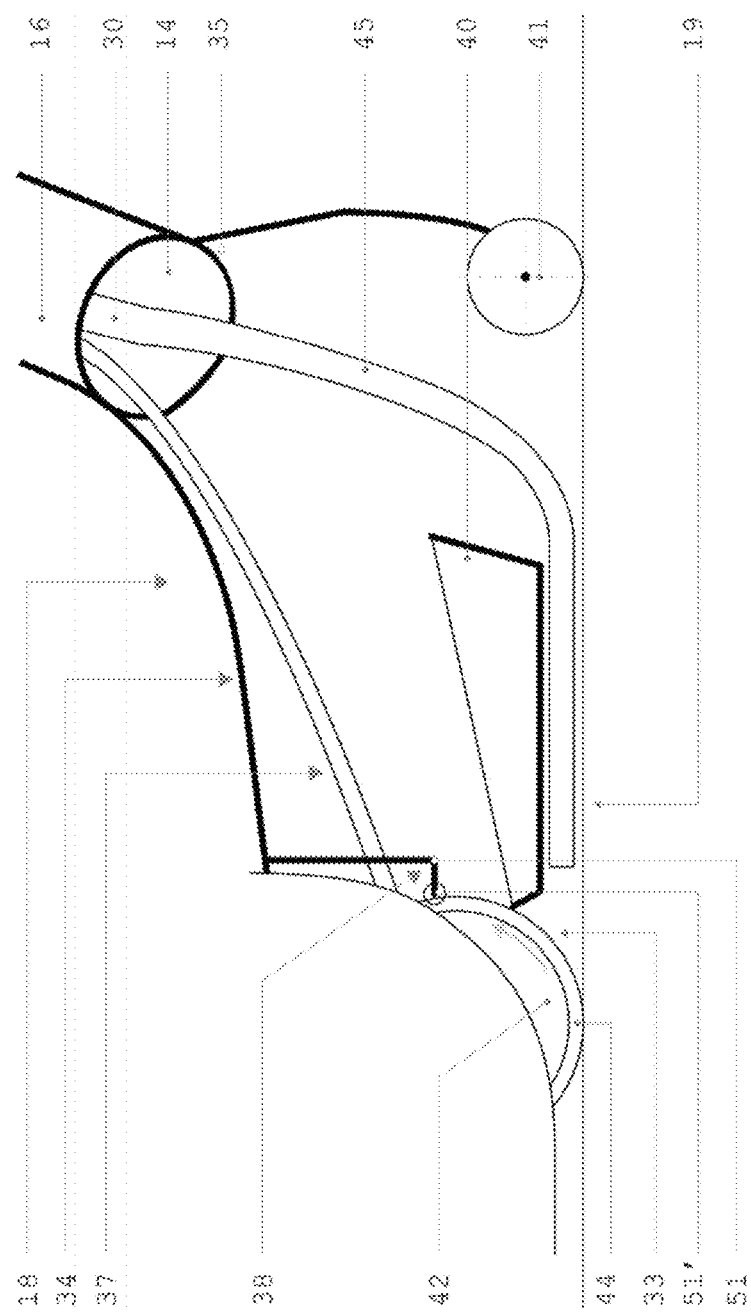
FIG. 10 shows a schematic cross-sectional view of a common part of the group of component elements of the above said three embodiments, in a second embodiment thereof, according to the invention.

Referring to FIGS. 3, 7, 9, which show a schematic cross-sectional view of the unit 18 of the device 15, respectively of a first, a second and a third embodiment thereof, and to FIG. 10, which shows a common part to above said three embodiments, in a second embodiment thereof, it may be noted that said unit 18 is constituted by a component elements assembly 33 inserted into a stiff shell-shaped casing 34, this latter being opened on its lower part and provided at its lower part with at least a free wheel 41, for allowing to move the device 15, and being provided on its upper part with an upper opening 35, in correspondence of the articulated joint 14, adapted to allow the connection between the component elements housed into the guiding body 16 and the component elements assembly 33, this latter being substantially constituted by at least a cleaning and sanitizing rotating motorized means 36 for surfaces 19, by one or more wetting and heating means 37 for said cleaning means 36, by at least a second cleaning means 38, adapted to maintain cleaned said first cleaning means 36, by at least an upper hollow container 40 for collecting the filth, adapted to collect the filth detached from the first cleaning means 36, by at least a sensor means 39 for detecting the moisture, adapted to measure the quantity of external moisture of said first cleaning means 36, for adjusting its wetting, and by a duct 45 for sucking the dried filth, as for example powder, form the surfaces 19.

Said rotating motorized means 36, as visible in FIGS. 4a-4c, is substantially constituted by a cylindrical-shaped rotating tool 42, arranged transversally in a rotating manner in the lower part of said casing 34 and with a rotating axis that is parallel to the surface 19, and is provided internally with an electrical means 43 of actuation in rotation, as for example an axial electrical motor, and externally is provided on its longitudinal surface with an absorbent coating element 44, constituted as for example by a lower multilayer sponge element 44', to which a microfiber fabric 44" is overlapped (See detail A in FIG. 4c).

Said moisture sensor means 39, constituted for example by sliding sensors made of conductive material, are arranged into contact on the surface of the absorbent coating element 44 (See FIGS. 4a-4b), preferably on the front part of the cylindrical rotating tool 42, and are also connected to the control and command electronic circuit board 22. With the device 15 in the operative state thereof, such moisture sensors 39 detects the moisture present on the coating element 44, while the cylindrical tool 42 rotates, sending later the detected value of the moisture to the electronic circuit board 22, in such a way that this later compares the received value with a pre-set value, pre-set thanks to the commands 20, and consequently it commands or not the additional wetting of the absorbent element 44 through the wetting and heating means 37, by actuating or not the electropump 27.

In particular, the detecting of the moisture on the absorbent coating element 44 is obtained by means of the reading of the electrical conductivity of the water present on the same absorbent element, in the way described below.

The electronic circuit board 22 reads the value of the electrical resistance (R) between two sensors made of conductive material 39 and it compares it with a reference value (X) pre-set thanks to actuation and selection means 20, and in case the element 44 is too dry, the electrical resistance value will be very high (R>X), and in this case the electronic circuit board 22 starts the electropump 27, that draws the water from the first reservoir 26 and conveys it to the surface of the absorbent element 44, thanks to the wetting and heating means 37, thus soaking it and increasing its electrical conductivity and reducing its electrical resistance (R).

The electropump 27 continues to work until the electrical resistance value measured between the sensors 39 equals or is lower than the reference value of the electronic circuit board 22 (R=X), and in this condition it turns off automatically.

When the electropump 20 is turned off, the coating element 44 is soaked with the desired quantity of water/moisture that is ideal for the desired cleaning operations.

During the use of the device 15, the quantity of water absorbed by the element 44 slowly decreases, while, as a consequence, the electrical resistance between the sensors 39 increases, thus getting back to the situation R>5 X and thereby repeating the starting cycle of the electropump 27, as described above.

Therefore, according to the X reference value stored in the electronic circuit board 22, the cleaning device 15 can provide the desired moisture level to the absorbent coating element 44, as for example a low moisture level for cleaning wooden or particularly sensitive surfaces, an average moisture level for cleaning smooth and glossy surfaces or a high moisture level for cleaning traditional, rough surfaces and the like.

Said upper hollow container 40 for collecting filth, adapted for collecting the filth detached from the first cleaning means 36, is constituted by a container open at the top thereof and of the removable type, and is fixed to the unit 18 in a lower position than the second cleaning means 38.

Said cut 45 for sucking the power is constituted by a is constituted by a stiff or semi-stiff pipe connected with one end portion thereof to the outlet of the duct 30 through the upper opening 35, possibly by means of a flow switch 54, and consequently to the second reservoir 29, whereas the other inlet end portion thereof 45' is opened and arranged in frontally in such a way to graze the surface 19, by sucking the powder present on the surface 19 by the use of the electrical vacuum means 32, which is actuated permanently by the electronic circuit board 22 when the device 15 is set in the operative state thereof, and by conveying later the powder into said second reservoir 29.

Said second cleaning means 38, adapted to maintain cleaned said first cleaning means 36 when the device 15 is set in the operative state thereof, in a first embodiment thereof, represented in FIGS. 3, 7, 9 and in particular in FIGS. 5a-5b, is constituted by at least an upper spring-loaded arm 51 fixed on the unit 18 and provided in the front part thereof with an upper roller 51' with horizontal axis and free rotation and by a lower collecting container 52, said roller 51' being made of stiff or semi-stiff material, as for example plastic or rubber, and with a length identical to or greater than the one of the cylindrical rotating tool 42 and arranged behind and parallel with respect to this latter, by maintained into contact against the coating element 44 thanks to the spring-loaded arm 51.

With this configuration, with the device 15 set in the operative state thereof while the cylindrical tool 42 rotates, the roller 51' rotates consequently thereby wringing the coating element 44, thus cleaning it and dropping the liquid and the filth into the lower container 52.

Said collecting container 52 is fixed and connect backwardly to a duct 53, that in turn is connected by using a flow switch 54 to the inlet of the duct 30 through the upper opening 35 and to the second reservoir 29, in such a way that the liquid and the filth collected into such container 52 be sucked and conveyed inside the second reservoir 29 by using the electrical vacuum means 32, that is activated by the electronic circuit board 22 when the device 15 is set in the operative state thereof.

Said flow switch 54, visible in detail in FIG. 6, constituted by a three-way chamber 54' containing a little tilting plate 55 hinged at an end portions thereof and commanded by a mechanical command 55' arranged on the upper external part of the casing 34, is adapted to lock selectively the suction flow of the duct 45 by letting free the suction flow from the container 52, or vice versa to lock the suction flow from the container 52 by letting free the suction flow of the duct 45.

Said second cleaning means 38, in the second embodiment thereof represented in FIG. 10, adapted to maintain cleaned the first cleaning means 36, is fixed in the unit 18, arranged above the container 40, and is constituted by at least an upper spring-loaded arm 51 provided in the front part thereof with an upper roller 51' with horizontal axis and free rotation and made of stiff or semi-stiff material, as for example plastic or rubber, with a length identical to or greater than the one of the cylindrical rotating tool 42 and arranged behind and parallel with respect to this latter, being maintained into contact against the coating element 44 thanks to the spring-loaded arm 51. With this configuration, with the device 15 set in the operative state thereof, while the cylindrical tool 42 rotates, the roller 51' rotates consequently thereby wringing the coating element 44, thus by cleaning it and dropping the liquid and the filth into the lower container 40.

Referring now to FIG. 3, in which it is shown the first embodiment of the unit 18, it may be noted that the wetting and heating means 37 of said first cleaning means 36 are constituted by at least an extended liquid delivering means 46, adapted to wet the upper part of the coating element 44, and by at least an heating element 47, adapted to heat the same coating element 44, such a liquid delivering means 46 and said heating element 47 activating themselves automatically, thanks to the electronic circuit board 22, when the device 15 is set in the operative state thereof, and subsequently being able to be deactivated and activated again in a selective way thanks to the commands 20.

Said delivering element 46 is constituted as for example by a duct 48 provided at its lower opened end portion with at least a delivering nozzle 49 and connected with its upper end portion to the to the duct 28 through the opening 35, said delivering nozzle 49 being arranged above and near to the rear part of said coating element 44, for wetting this latter with the liquid that is pumped by the electropump 27, in the way and with the quantities already previously described, thanks to the moisture sensor means 39.

Said heating element 47 is constituted by a body 56 made of aluminium and shaped for following the shape and dimensions of the upper part of the cylindrical rotating tool 42 and arranged into contact on it, and is provided with at least an electrical resistance 57, and with a temperature detecting and regulating means 58, as for example a thermostat or a thermistor of the NTC type, which are connected to and commanded by the electronic circuit board 22. Said electrical resistance 57 is adapted to heat the body made of aluminium 56 that in turn heats for contact the coating element 44, while said temperature detecting and regulating means 58 is adapted to detect continuously the temperature of the body made of aluminium 56 by activating or deactivating automatically said resistance 57, on the basis of the temperature value pre-set on the electronic circuit board 22, thanks to the commands 20, in such a way to maintain or to interrupt the heating of the body made of aluminium 46, and thus by maintaining the coating element 44 at the desired temperature, with a maximum of 130° C.

Referring now to FIG. 7, in which it is shown the second embodiment of the unit 18, it may be noted that the wetting and heating means 37 of said first cleaning means 36 are constituted by a first steam generator element 59, controlled and commanded by the electronic circuit board 22, and connected with its inlet through a duct 60 the duct 28 through the upper opening 35 and with its outlet to at least a liquid and/or steam delivering means 61, that in turn is arranged spaced away above the upper part of the cylindrical rotating tool 42, and adapted to deliver liquid and/or steam on the coating element 44 for wetting this latter with liquid, possibly vaporized, pumped by the electropump 27 while the device 15 is set in the operative state thereof and in the way and with quantities already previously described, thanks the moisture sensor means 39.

Figure 8A:
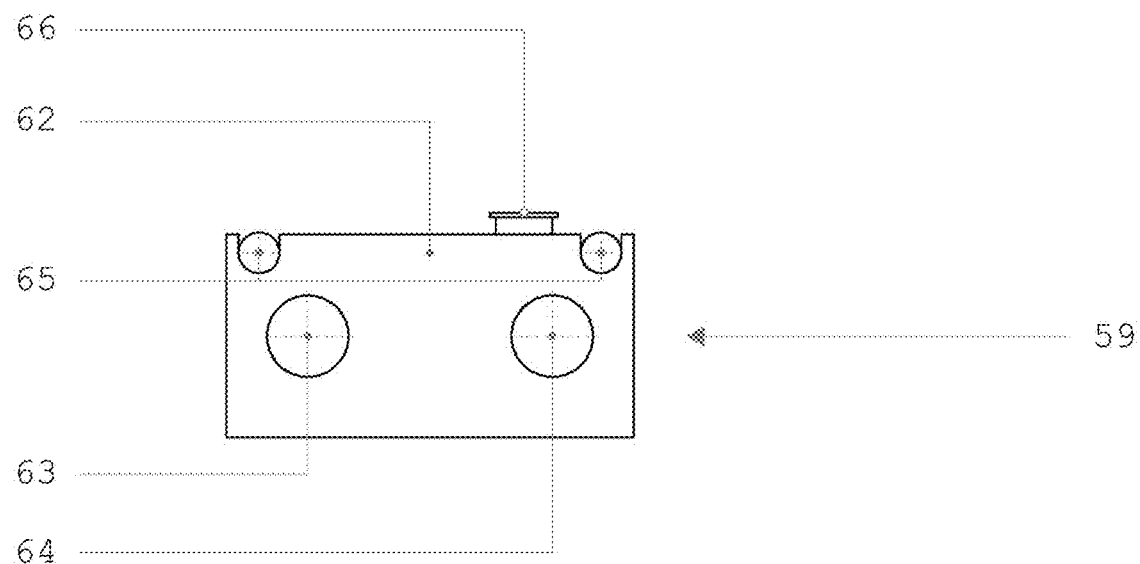
FIG. 8a shows a front view of an element of the group of FIG. 7.
Figure 8B:
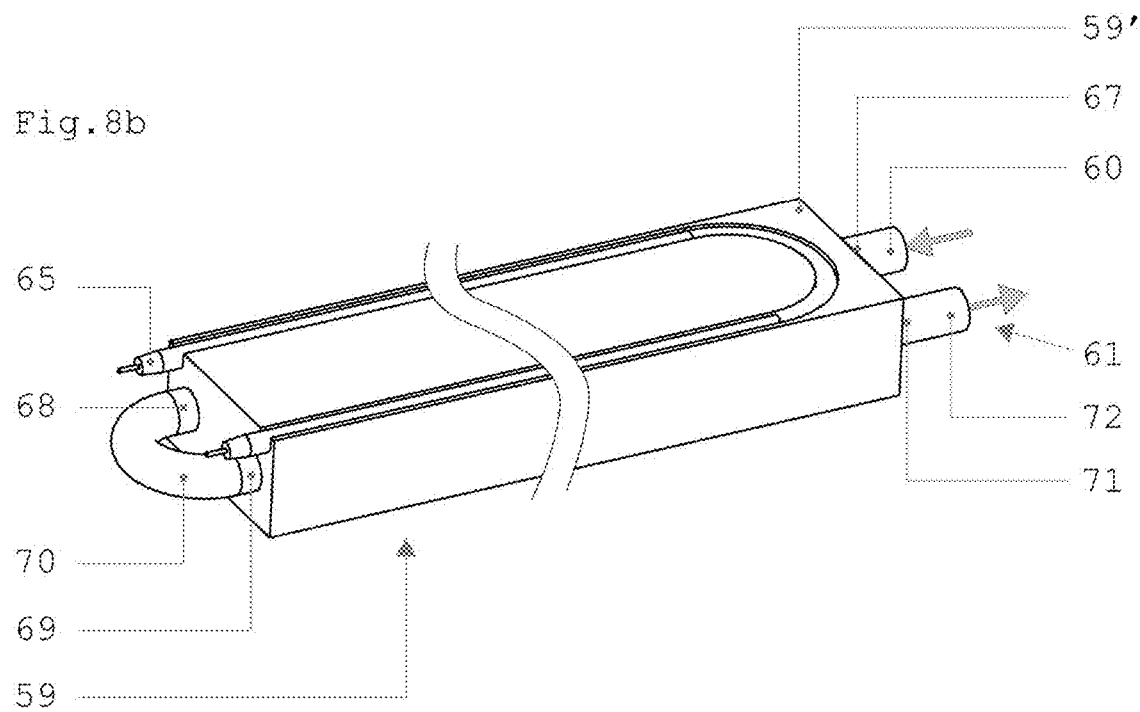

Said steam generator means 59, represented in detail in FIGS. 8a-8b, is constituted by an heating element 59', realized with a body 62 made of metal, preferably of aluminum, provided with at least two internal through ducts 63, 64 spaced away to each other, with at least an electrical resistance 65 that covers at least the path of two said ducts 63, 64 and with the temperature detecting and regulating means 66, as for example a thermostat or a thermistor of the NTC type, that together the resistance 65 is connected to and commanded by the electronic circuit board 22 for the automatic control of the temperature.

Such a steam generator 59 activates automatically thanks to the electronic circuit board 22, when the device 15 is set in the operative state thereof, and subsequently is able to be deactivated and activated again in a selective way thanks to the commands 20.

The first duct 63 is joined with its inlet 67 to the duct 60 and with its outlet 68 to the inlet 69 of the second duct 64, through a pipe 70 or equivalent, whereas the outlet 71 of the second duct 64 is joined to the inlet 72 of the steam delivering element 61, which follows the shape and dimensions of the upper part of the cylindrical rotating tool 42, furthermore it is inside hollow and is provided with at least a lower delivering nozzle (not shown) turned on to the coating element 44.

The water drawn from the first reservoir 26 thanks the electropump 27, when the device 15 is set in the operative state thereof, is converted in steam inside the body 62 made of metal and consequently the steam is directed on to the coating element 44 through the delivering nozzles of the delivering element 61, by maintaining a desired unvaried temperature thanks to the temperature detecting and regulating means 66, which detects continuously the temperature of the body 62 made of metal by activating or deactivating said resistance 65, on the basis of the temperature value pre-set into the electronic circuit board 22 thanks to the commands 20, in such a way to maintain or to interrupt automatically the heating of the body 62 made of metal, and so by generating or not steam, maintaining said coating element 44 at a desired temperature, up to a maximum of 130° C.

Referring now to the FIG. 9 only, in which it is shown the third embodiment of the unit 18, it may be noted that the wetting and heating means 37 of said first cleaning means 36 are constituted by at least an extended liquid delivering element 73, adapted to wet the upper part of the coating element 44 and by at least a heating element 74, adapted to heat the same coating element 44.

Said delivering means 73 is constituted as for example by a pipe 75 provided at its lower opened end portion with at least a delivering nozzle 76, and connected with its other end portion to the duct 28 through the upper opening 35, said delivering nozzle 76 being arranged near the rear part of said cylindrical tool 42, for be able to wet the coating element 44 with the liquid pumped by the electropump 27, in the way and with the quantities already previously described, thanks to the moisture sensor means 39.

Said heating element 74 is arranged spaced away above the cylindrical rotating tool 42 and is constituted by a semi-circular reflecting parabolic dish 77, made of metal, as for example aluminum, and with the concave part 78 thereof turned downward, and provided with an electrical incandescence resistance 79, adapted to heat by radiation the coating element 44, and with a temperature detecting and regulating means 80, as for example a thermostat or a thermistor of the NTC type, and adapted to detect continuously the temperature of said parabolic dish 77, said thermostat 80 detecting continuously such a temperature and sending it to the electronic circuit board 22, in such a way that this latter may compare it with a temperature value pre-set thanks to the commands 20 and automatically may activate, maintain or interrupt the heating, thanks to the electrical resistance 79, maintaining said coating element 44 at the desired temperature, up to a maximum of 130° C. said heating element 74 activates automatically, thanks to electronic circuit board 22, when the device 15 is set in the operative state thereof, and subsequently is able to be deactivated and activated again in a selectively way thanks to the commands 20.

Said parabolic dish 77 is also provided with an external peripheral thermal-insulating layer 81 and with a protection made of ceramic glass 82 arranged under the concave part 78.

Said device 15, may be also used in a cold way by deactivating selectively, with the commands 20, the heating element 47, 74 or the steam generator element 59, according the embodiment of the same device, or may be used only as a vacuum cleaner, by activating by the use the commands 20 the electrical vacuum means 32 only.

Finally, said device 15 is powered by the use of a power cord 24 connected to the household power grid or alternatively by the use of an internal battery 25, if the above said power cord 24 is not connected to the household power grid.

Such a internal battery 25 is of the rechargeable type, and charges automatically by the use of the electrical transformer 23 while the device 15 is connected with the power cord 24 to the household power grid.

The invention claimed is:

1. A hand-guided treatment device for walkable surfaces, adapted to clean, to sanitize and to dry such surfaces, comprising a guiding body extended upward and ending with a control handle and joined below through an articulated element, to a unit for cleaning, sanitizing and drying such surfaces, the handle being provided with command means for such a treatment device, said guiding body having housed inside it at least a control and command electronic circuit board, which is adapted to control and to command all the electric and electronic elements and components and means of the treatment device, which are selected through said command means, and being powered by at least an electrical transformer means, which in turn is connected to a power grid through a power cable, at least a first reservoir and at least an electrical pumping means, being also housed into said guiding body and connected to said electronic circuit board and to the electrical transformer, said unit comprised of a component elements assembly inserted into a stiff and shell-shaped casing, the latter being opened on its lower part and provided at its lower part with at least a free wheel, for allowing movement of the treatment device, and being provided on its upper part with an upper opening, in correspondence of the articulated element, adapted to connect component elements of the guiding body and said component elements assembly, wherein the component elements assembly comprises at least a first cleaning, sanitizing and drying rotating motorized means for surfaces, one or more wetting and heating means, arranged on the upper and back part of said first cleaning means, at least a second cleaning means arranged into contact with the rear part of said first cleaning means, at least a container for collecting filth, arranged on the rear part of said first cleaning means, at least a sensor means for detecting the moisture, arranged into contact with the front part of said first cleaning means, said rotating motorized means comprising a cylindrical-shaped rotating tool, arranged in a rotating manner in the lower part of said casing and with a rotating axis that is parallel to the surface, and being provided internally with an electrical means of actuation in rotation, and externally being provided on its longitudinal surface with an absorbent coating element, in such a way that the cylindrical rotating tool rotates, actuated at least in one direction of motion by the electrical means of actuation in rotation, by remaining in contact with the surface with its lower longitudinal profile, while the treatment device in the operation state thereof is moved, thereby being able to rub efficaciously said surface, said wetting and heating means comprising at least a delivering element and at least a heating element, this latter including in turn at least a temperature detection and regulating means, at least said first reservoir being adapted to contain the cleaning liquids, being connected with its outlet to the electrical pumping means, in turn connected to the delivering element, in such a way to draw the liquid from said first reservoir and to convey such a liquid to the coating element of the rotating tool, while said heating element being adapted to heat automatically the coating element at a pre-set temperature by cooperating with the electronic circuit board facilitated by the temperature detection and regulating means, comprising a thermostat or a thermistor of the NTC type, cooperating with the same electronic circuit board in such a way that the latter selectively activates the heating, said moisture sensor means being adapted to detect the moisture present in the coating element, while the cylindrical tool rotates, by cooperating with the electronic circuit board, in such a way that the latter selectively commands the additional wetting of the absorbent coating element through the wetting and heating means on the basis of a pre-set moisture value, said second cleaning means being adapted to wring out the coating element of the rotating tool, to let fall the filth in at least a lower container.

2. Device according to claim 1, wherein said coating element comprises a lower multilayer sponge element, to which a microfiber fabric is overlapped.

3. Device according to claim 1, wherein said delivering element comprises a pipe provided at its lower opened end portion with at least a delivering nozzle and connected with its upper end portion to the electrical pumping means, said delivering nozzle being arranged above and near to the rear part of said coating element, for wetting the latter with the liquid that is pumped by the same electrical pumping means, and wherein said heating element comprises a body made of aluminium and shaped for following the shape and dimensions of the upper part of the cylindrical rotating tool and arranged into contact on it, and is provided with at least an electrical resistance, and with the temperature detecting and regulating means, which are connected to and commanded by the electronic circuit board, in such a way that said electrical resistance is adapted to heat the body made of aluminium that in turn heats for contact the coating element, while said temperature detecting and regulating means detects continuously the temperature of the body made of aluminium by activating or deactivating automatically said resistance, on the basis of the temperature value pre-set on the electronic circuit board, thanks to the command means.

4. Device according to claim 1, wherein said heating means is a steam generator means, controlled and commanded by the electronic circuit board, connected with its inlet to the electrical pumping means and at its outlet to said delivering element, which is provided with at least a lower delivering nozzle, that in turn is arranged spaced away above the upper part of the cylindrical rotating tool, by following its shape and dimensions, and is adapted to deliver steam on the coating element, and wherein said heating element is realized with a body made of metal, as for example aluminum, provided with at least two internal through ducts spaced away to each other, with at least an electrical resistance that covers at least the path of two said ducts and with the temperature detecting and regulating means, that together the resistance is connected to and commanded by the electronic circuit board for the automatic control of the temperature, the first duct being joined with its inlet, through pipes, to the electrical pumping means and with its outlet to the inlet of the second duct, through a pipe or equivalent, whereas the outlet of the second duct being joined to an inlet of the delivering element, in such a way that, the water drawn from the first reservoir facilitated by the electrical pumping means is eventually converted into steam inside the body made of metal and consequently directed on the coating element through the lower delivering nozzles of the delivering element, by maintaining a desired unvaried temperature thanks to the temperature detecting and regulating means, which detects continuously the temperature of the body made of metal by activating or deactivating said resistance, on the basis of the temperature value pre-set into the electronic circuit board according to the command means.

5. Device according to claim 1, wherein said delivering element is constituted by a pipe provided at its lower opened end portion with a delivering nozzle, and is connected with its other end portion to, through pipes, to the electrical pumping means, said delivering nozzle being arranged near the rear part of said cylindrical rotating tool, to wet the coating element with the liquid pumped by said electrical pumping means, and that said heating element is arranged spaced away above the cylindrical rotating tool and is constituted by a semi-circular reflecting parabolic dish with the concave part thereof turned downward, and made of metal, as for example aluminum, and provided with an electrical incandescence resistance, adapted to heat by radiation the coating element, and with a temperature detecting and regulating means, this latter detecting continuously such a temperature of said parabolic dish by activating or deactivating automatically said resistance, on the basis of the temperature value pre-set into the electronic circuit board according to the command means.

6. Device according to claim 1, wherein said second cleaning means is arranged above the container and comprises at least an upper spring-loaded arm provided in the front part thereof with an upper roller with free rotation about its horizontal axis and made of stiff or semi-stiff material, with a length identical to or greater than the one of the cylindrical rotating tool and arranged behind and parallel with respect to the latter, by maintained into contact against the coating element as facilitated by the spring-loaded arm.

7. Device according to claim 1, wherein at least a second reservoir is also housed into the guiding body, arranged in a lower position with respect to the first reservoir, and is connected with its outlet at least to an electrical vacuum means, in turn connected to and commanded by the electronic circuit board, said second reservoir being connected with its inlet to the outlet of two ducts arranged into the cleaning unit, in such a way that the electrical vacuum means sucks possible remaining filth, as powder, after the treatment of the surface and by conveying such filth into said second reservoir, while the treatment device is set in the operative state thereof.

8. Device according to claim 7, wherein said duct comprises a stiff or semi-stiff pipe with its inlet opened and arranged frontally so as to graze the surface.

9. Device according to claim 7, wherein said second cleaning means is constituted at least by an upper spring-loaded arm fixed to the cleaning unit and provided frontally with an upper roller with free rotation about its horizontal axis and under which the lower collecting container is arranged, said roller being realized of stiff or semi-stiff material, with the length identical to or greater than the one of the cylindrical rotating tool and arranged behind and parallel with respect to the latter, being maintained in contact against the coating element by way of the spring-loaded arm, said container being fixed and connected at its back part, through said duct, to the second reservoir, in such a way that the liquid and the filth collected into such reservoir are sucked and conveyed into said second reservoir through the electrical vacuum means, while the treatment device is set in the operative state thereof.

10. Device according to claim 7, wherein said ducts are both connected to said second reservoir by means of a flow switch, which comprises a three-way chamber containing a little tilting plate hinged at its end portions and commanded by a mechanical command arranged on the upper external part of the casing, the plate being adapted to lock selectively the suction flow of the duct by letting free the suction flow from the container through the duct, or vice-versa to lock the suction flow from the container by letting free the suction flow of the duct.

11. Device according to claim 1, wherein it is electrically powered through the use of the power cable connected to the power grid or through the use of an internal battery of the rechargeable type, arranged into said guiding body, such internal battery recharging automatically through the electrical transformer while the treatment device is connected with the power cable to the power grid.

* * * * *